US008454909B2

(12) United States Patent
Martinell Gispert-Sauch

(10) Patent No.: US 8,454,909 B2
(45) Date of Patent: Jun. 4, 2013

(54) DEVICE FOR LOADING REAGENT CARDS FOR CLINICAL ANALYSERS

(75) Inventor: Enrique Martinell Gispert-Sauch, Barcelona (ES)

(73) Assignee: Grifols, S. A. (ES)

(*) Notice: Subject to any disclaimer, the term of this patent is extended or adjusted under 35 U.S.C. 154(b) by 521 days.

(21) Appl. No.: 11/873,126

(22) Filed: Oct. 16, 2007

(65) Prior Publication Data

US 2008/0098830 A1 May 1, 2008

(30) Foreign Application Priority Data

Oct. 31, 2006 (ES) .................................. 200602766

(51) Int. Cl.
*B65D 1/34* (2006.01)
*B01L 9/00* (2006.01)

(52) U.S. Cl.
USPC ............................. 422/561; 422/563; 206/564

(58) Field of Classification Search
USPC ............................. 206/560, 561, 563; 422/563
See application file for complete search history.

(56) References Cited

U.S. PATENT DOCUMENTS

| 3,756,383 | A | * | 9/1973 | Kryter ....................... 206/387.14 |
| 4,673,088 | A | * | 6/1987 | Mancini ....................... 211/70.5 |
| 4,722,453 | A | * | 2/1988 | Hamilton ....................... 220/533 |
| 5,975,314 | A | * | 11/1999 | Lee ............................... 211/13.1 |
| 2006/0029524 | A1 | | 2/2006 | Carter et al. |

FOREIGN PATENT DOCUMENTS

| EP | 0081829 | 6/1983 |
| EP | 0895087 | 2/1999 |
| ES | 2150339 | 11/2000 |
| GB | 1205752 | 9/1970 |
| WO | 2006/043181 | 4/2006 |

OTHER PUBLICATIONS

Notification of Reason for Refusal issued Aug. 27, 2010 in JP 2007-282659 with English Language translation.

* cited by examiner

*Primary Examiner* — In Suk Bullock
*Assistant Examiner* — Paul Hyun
(74) *Attorney, Agent, or Firm* — RatnerPrestia

(57) ABSTRACT

The device comprises a support in the form of a tray or the like, which is at the top and provided inside with first grooves for guiding first cards arranged parallel to each other, forming a single level for the cards and is characterized in that it has sets of grooves interposed between the first grooves, allowing a second level of cards to be placed at a level higher than the first cards.

9 Claims, 7 Drawing Sheets

DEVICE FOR LOADING REAGENT CARDS FOR CLINICAL ANALYSERS

CROSS-REFERENCE TO RELATED APPLICATIONS

This application claims priority to Spanish patent application Ser. No. 200602766, filed Oct. 31, 2006, the entire content of which is hereby incorporated by reference.

The present invention relates to a device for loading reagent cards for clinical analysers. The device is also used for transporting and storing the cards.

Clinical analysis cards consist of a support element provided with various microtubes or small cups of variable cross-section from the upper opening to the closed lower end, incorporated in a flat support, which joins them together. The usual form of storage and transport of said cards consists of open supports provided with grooves in which the cards are interposed, which are placed side by side and for practical purposes occupy the total volume of the support, which generally takes the structure of a tray open at the upper face. The grooves for guiding the cards are produced on the inner faces of the lateral walls of the box or tray and allow said cards to be guided into position and reduce the vibrations and movement to which they are subjected during transport. Said boxes may be used directly by automatic analysis machines, so that the roboticised devices of said machines are able to take each card individually from successive boxes.

A feature of said boxes or trays for containing the cards lies in the separation of each card from the next one, leaving a predetermined space to allow the roboticised mechanisms of the automatic analysis machine to operate. Therefore, the number of cards contained in a tray designed to hold them is limited by the width of the cards and the minimum separation needed between each two successive cards, and account must be taken of the fact that the volume occupied by the number of cards contained in a box is significant from the point of view both of storage capacity in the clinical analysis machine and the space occupied in thermostatically controlled areas to maintain the cards at the reaction temperatures selected for the analyses.

It would clearly be of great interest to be able to increase the number of cards that can be stored in a storage and transport tray of currently known type in order to thus have a greater number of cards available for the same volume of the components contained in the machine, from the point of view both of handling and thermostatically controlled processing. To summarise, the preferred objectives are as follows:

- to increase the load or storage capacity in the machine;
- to reduce the volume for the transport and logistical distribution of the product;
- to reduce the volume in logistics warehouses and at the premises of the end customer, especially when there is a requirement for the product to be refrigerated (laboratory refrigerator or similar).

To achieve this objective, the inventors have designed a device comprising a tray carrying cards for clinical analysers that allows the number of cards per unit of plan area of the tray containing them to be doubled, which is a practical way of doubling the number of cards that can be arranged in the areas of the machine designed for this purpose, which doubles the capacity of said areas. The basis of the invention is the arrangement of the cards in the tray containing them in two distinct levels, separated by a small vertical distance, so that to handle the cards, the automated selection and transport mechanisms of the analysis machine first handle the cards from the top level and then those from the lower card level, which is not a problem for the automated components of said machines. To achieve this objective, apart from the usual grooves on either side of the side walls of the tray designed to receive the corresponding cards, the tray will have other card centring grooves arranged in an intermediate position with regard to the first, for receiving other cards which will be placed between the first cards, in other words, with those cards conventionally placed in a support tray and which will be supported vertically by resting on the trays of the lower level or possibly by resting on special abutment areas produced in the bottom of the tray. It will be understood that since there are new grooves in the mid-position between the two other grooves already present in the tray, the separation between each two successive cards comprising the upper or second level will be equal to those in the lower or first level, and there will therefore be no difficulty in handling the cards.

It will be understood that by producing the card loading device according to the present invention, the number of cards per unit of tray area will be doubled and the slight increase in height occupied by the cards in the upper level will not constitute a drawback since, given the conventional measurements of said cards, the excess height of several millimeters of the cards in the upper level will not be a drawback in handling or storage.

Maximum use will be made of the plan area of the tray since the projection in vertical direction of all the cards in the first and second levels is at least equal to the total area of the bottom of the tray.

The invention will be better understood through the accompanying drawings, given as an explanatory, but not limiting example of the device for loading reagent cards for clinical analysers that is the object of the present invention.

Figure 7:
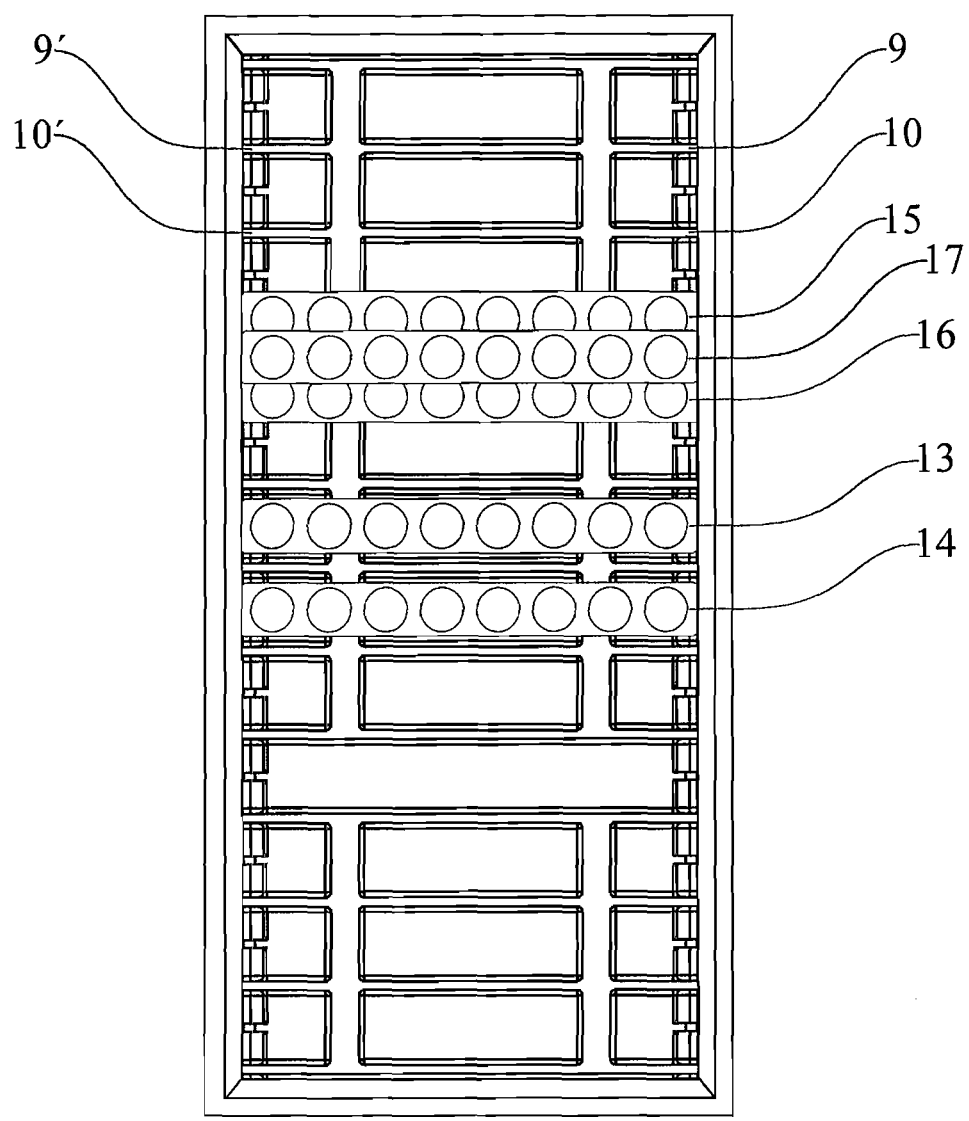

For a better understanding, FIG. 7 shows a plan view of the device according to the present invention with cards placed therein.

Figure 5:
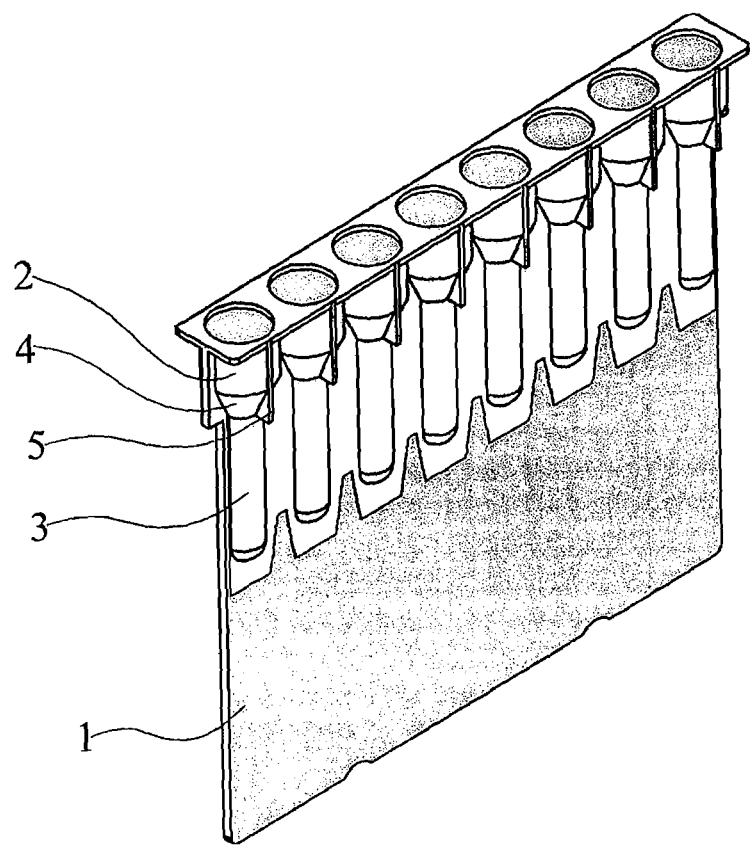
FIG. 5 shows a perspective view of a card of conventional design for clinical analyser apparatus.
Figure 6:
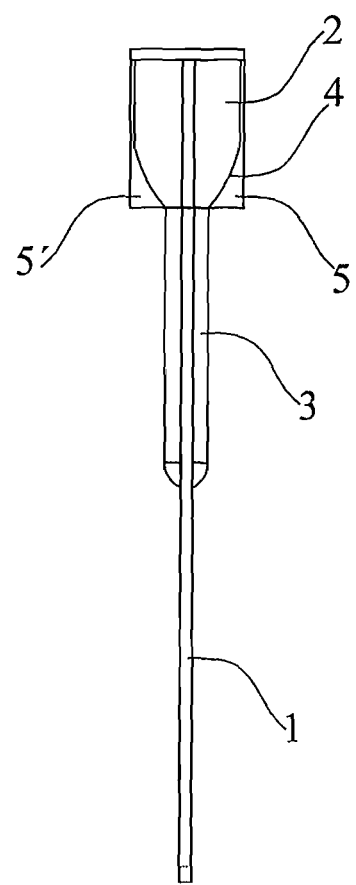
FIG. 6 shows a view in side elevation of the card shown in FIG. 5.

Cards for clinical analysis apparatus comprise, as shown in FIGS. 5 and 6, a laminar support 1 on which multiple microtubes or small cups are arranged in succession in a row, each one comprising an upper chamber 2 of somewhat larger diameter than the rest and a lower tubular element 3 of smaller diameter, with an intermediate joining cone 4. The upper part comprising the cylindrical chamber 2 and the cone 4 conventionally has ribs or external laminar projecting elements 5 which may perform a support function on the handling elements of the analysis apparatus.

Clearly, said ribs 5 will be arranged on each of the two sides of the card, as can be seen in FIG. 6, in which a laminar projection 5 has been illustrated on one of the sides and a laminar projection 5', which is symmetrical in relation to the first one, on the other side of the card.

The device according to the present invention basically comprises a body 6 of rectangular plan structure, provided with side walls 7 and 8 in which the usual grooves for receiving the clinical analysis cards are formed, as indicated by the numerals 9, 10, 11, 12, etc. which are repeated on the opposite side face, as can be seen in FIG. 7, in which the grooves 9" and 10" of the wall 7 opposite to the grooves 9 and 10 of the wall 8 have been illustrated. This allows the cards to be placed in the usual way, as can be seen for the cards indicated by the numerals 13 and 14 in FIG. 7, leaving a specific space between each two adjacent cards to allow them to be handled.

According to the present invention, between each two grooves of the usual type 9, 10, 11, 12, etc. supplementary grooves such as 9", 10", 11", 12" etc. are arranged, each of which is situated at an equal distance from the two principal mutually adjacent grooves, for example, groove 10" is situated at an equal distance from the adjacent grooves 9 and 10.

Figure 1:
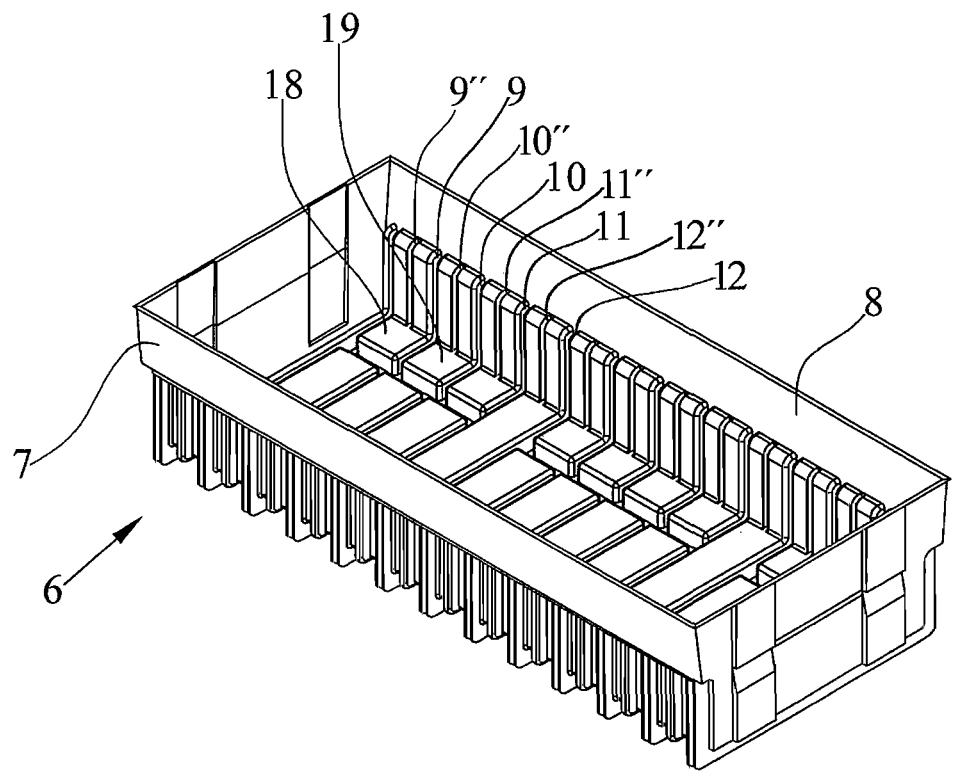
FIG. 1 shows a perspective view of the device for loading cards that is the subject of the present invention.
Figure 2:
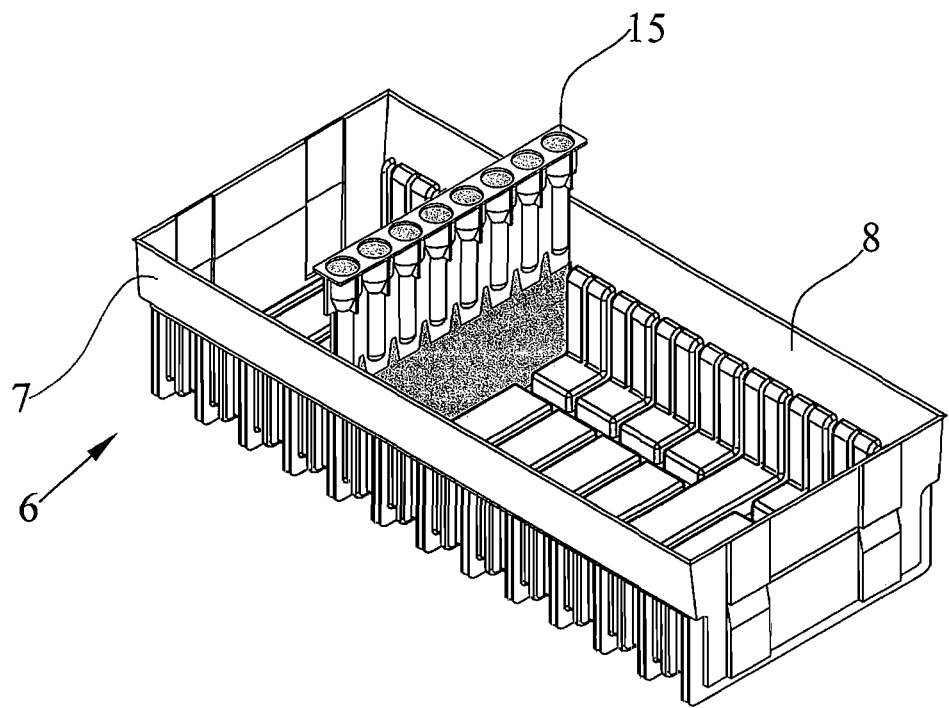
FIG. 2 shows a perspective view of the device for loading cards according to the present invention with a first card incorporated therein, corresponding to a low level.
Figure 3:
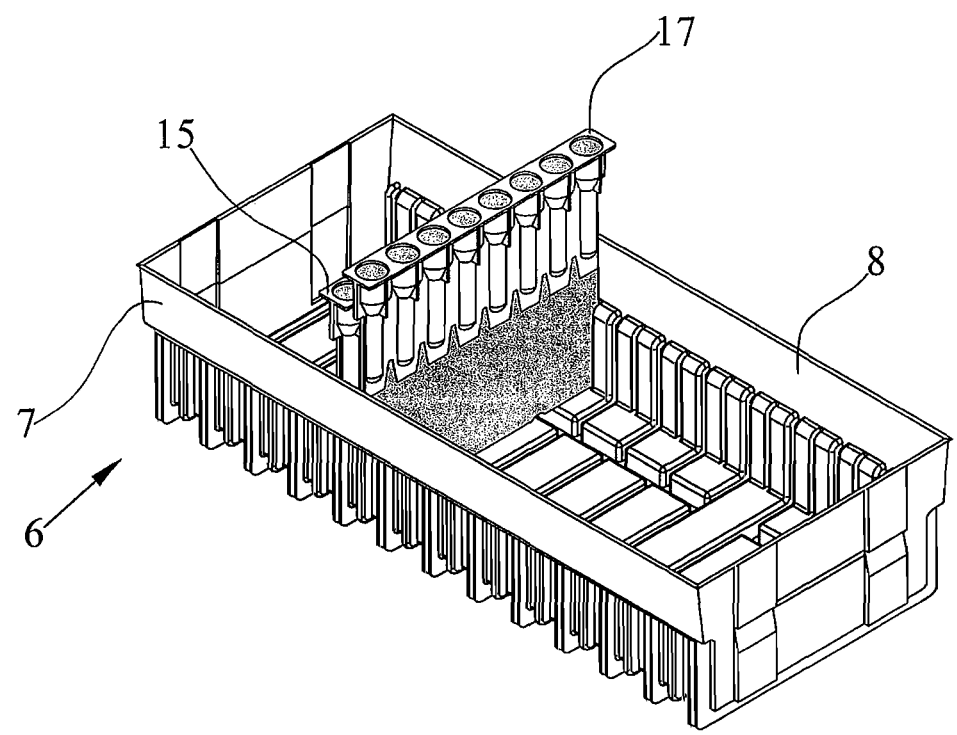
FIG. 3 shows a similar view to FIG. 2 with a card arranged in the intermediate position, corresponding to the high level.
Figure 4:
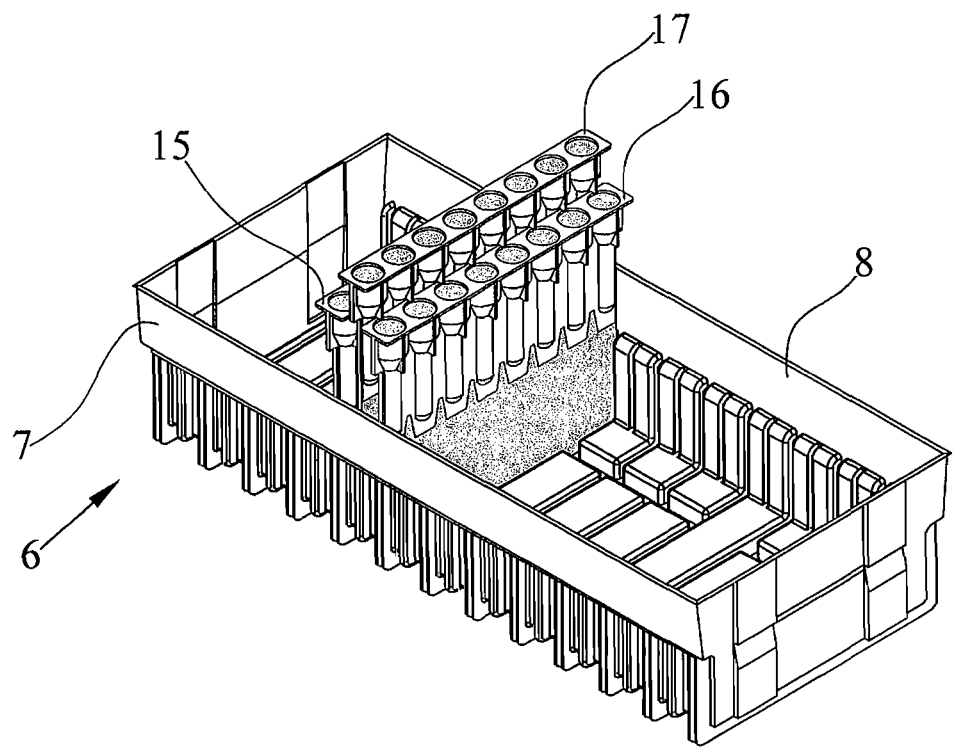
FIG. 4 shows a similar view to FIGS. 2 and 3 with a third card arranged adjacent to those previously arranged, corresponding to the low level.

By means of this arrangement it is possible to place a card at a higher level between each two cards arranged conventionally, which have a lower level, as can be seen in FIG. 4, in which the cards 15 and 16 can be seen in the conventional arrangement and card 17 interposed between said cards 15 and 16, being guided by the grooves in the sides of the tray arranged between the conventional guiding grooves. The cards on the upper level, such as card 17, will be guided by the grooves and will be supported and abutted in their lower region by side ribs against the upper face of the immediate cards 15 and 16, as can be seen in FIG. 4, or they may abut the lower part of the grooves for the cards in the upper level, in other words, the grooves 9", 10", etc. in which the lower abutment blocks such as 18 and 19 in FIG. 1 may be of a suitable height to establish said lower abutment.

The device according to the present invention also comprises an upper closure cover to protect the cards from the atmosphere during storage and transport, both from damp and from particles or dust that could affect their functionality.

Although the invention has been described with reference to an example, which has been illustrated and described, it will be understood that many variants may be introduced in producing the invention based on the subject matter that has been disclosed, which will form part of the invention provided that they are included within the scope of the accompanying claims.

The invention claimed is:

1. A support device for clinical analyzer reagent cards, comprising: two opposing side walls and two opposing end walls, wherein interior surfaces of the opposing side walls comprise:
   a) a first set of corresponding vertical grooves, each groove terminating at a first abutment surface having. a first height; and
   b) alternating with the first set of grooves, a second set of corresponding vertical grooves, each groove terminating at a second abutment surface having a second height, the second abutment surface extending between adjacent grooves of the first set,
   wherein said vertical grooves are configured to accept clinical analyzer reagent cards and wherein a width of each groove of the first set and the second set is substantially the same.

2. The device of claim 1, wherein the opposing side and end walls form a rectangular structure.

3. The device of claim 1, wherein the first set of grooves and the second set of grooves are configured to accept reagent cards in a parallel orientation relative to the end walls.

4. The device of claim 3, wherein the second set of cards at a second height rest on a bottom edge of the second abutment surface of the support.

5. The device of claim 3, wherein the reagent cards in the support are arranged at alternating heights corresponding to said first height and said second height.

6. The device of claim 1, wherein the grooves of the second set of grooves are spaced an equal distance from adjacent grooves of the first set of grooves.

7. The device of claim 1, wherein the grooves of the second set of grooves are spaced from the grooves of the first set of a grooves a distance less than the maximum width of the reagent cards.

8. A support device for introducing reagent cards to a clinical analyzer, comprising;
   reagent cards in a support comprising two opposing side walls and two opposing end walls, wherein interior surfaces of the opposing side walls comprise:
      a) a first set of corresponding vertical grooves, each groove terminating at a first abutment surface having a first height; and
      b) alternating with the first set of grooves, a second set of corresponding vertical grooves, each groove terminating at a second abutment surface having a second height, the second abutment surface extending between adjacent grooves of the first set, and
   wherein said vertical grooves are configured to accept the reagent cards,
   wherein the sequentially loaded reagent cards in the support are arranged at alternating heights corresponding to said first height and said second height, and
   wherein a width of each groove of the first set and the second set is substantially the same.

9. The device of claim 8, wherein the reagent cards loaded into the device are oriented parallel to the end walls.

* * * * *